United States Patent [19]

Sommer et al.

[11] Patent Number: 4,677,205
[45] Date of Patent: Jun. 30, 1987

[54] CHEMICAL AGENT

[75] Inventors: Harold Z. Sommer, Havre de Grace; George E. Wicks, Jr., Baltimore, both of Md.

[73] Assignee: The United States of America as represented by the Secretary of the Army, Washington, D.C.

[21] Appl. No.: 628,226

[22] Filed: Mar. 29, 1967

[51] Int. Cl.[4] .......................................... C07D 213/69
[52] U.S. Cl. ...................................... 546/292; 546/13
[58] Field of Search ............................ 260/296, 482 C; 167/33 D, 47; 424/263; 546/292, 13

[56] References Cited

U.S. PATENT DOCUMENTS 3,188,955  6/1965  Brown .................................. 102/24

OTHER PUBLICATIONS

Mathes et al., Angew Chem., Intern, Ed. English, vol. 2, pp. 144–149 (1963).

Primary Examiner—John F. Terapane
Assistant Examiner—John S. Maples
Attorney, Agent, or Firm—Anthony T. Lane; Robert P. Gibson; Harold H. Card, Jr.

[57] ABSTRACT

New chemical compounds having the generic formula:

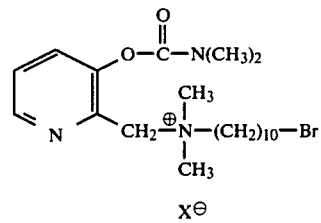

wherein X is one equivalent of an anion selected from the group consisting of monovalent or polyvalent anions, and having utility as incapacitating agents and in munitions.

3 Claims, No Drawings

CHEMICAL AGENT

SPECIFICATION

This invention relates to the synthesis of new toxic chemical compounds which are useful as a chemical warfare agent. More particularly, our invention is concerned with novel compounds produced by means of a quaternizing reaction.

These chemical agents act mostly on the peripheral autonomic cholinergic nerve system which includes the motor nerves, the preganglionic fibers, the ganglia, the post-ganglionic parasympathetic fibers, and neuromuscular functions. The transmission of impulses along a nerve or from nerve fibers or secretory cells or from one nerve fiber to another across synapses in ganglia is thought to involve chemical changes either directly or as the source of potential differences.

Quaternary ammonium compounds in general are known to be physiologically active materials. Mainly because of their positively charged "onium" centers they are attracted by anionic sites in animal tissues, particularly those situated at cell surfaces and interfaces. They can induce physiological responses that mimic or antagonize the action of acetylcholine as a result of their interaction with the various physiological receptor sites of acetylcholine, especially those at membranes of muscle cells. They also combine with enzymes such as acetylcholinosterase, other esterases, acetylcholineacetylase, etc., thus inhibiting their participation in the biological processes.

One of the significant anatomical differences between the neuromuscular junctions and other acetylcholine receptive sites is the absence of a membrane barrier or a sheath such as envelops the gangalia. The ease of accessibility of the neuromuscular junctions to "onium" compounds contributes to their relatively fast onset of action and partly explains why in many instances relatively small doses suffice to evoke physiological actions that modify or interrupt normal neuromuscular impulse transmission.

Depending on their chemical structures different quaternary compounds interfere with the mechanism of impulse transmission in different manners and the final physiological effects can vary considerably. Some quaternary ammonium compounds are used as therapeutic agents, others are known to be lethal. The magnitude, accessibility, and distribution of the positive charges in quaternary compounds are believed to be the key factors in the determination of specificity of action. Recognition of these facts explain the strikingly different physiological behavior so often observed when structurally very closely related compounds are compared. The nature of the groups attached to the quaternary nitrogens influences the distribution of the cationic charges. The length and branching of aliphatic chains and the volume and configuration of aromatic and alicyclic rings have a bearing on the difficulty of approach to the specific receptor sites. Electrophilic and necleophilic centers in the molecule will insert their inductive effects on the positive charges and can also aid in the interaction with the "esteratic sites" of various enzymes. These sites are believed to be located in close vicinity to the anionic sites of the active centers. Substitution of different functional groups influence association and hydration and may considerably change the solubilities in physiological media. In bis-quaternary and poly-quaternary compounds, the distance between the electric charges must be considered. These factors contribute to governing the rate and reversibility of the chemical reactions involved, and which determine the final physiological responses.

Our chemical agents interfere with the normal process of neuromuscular impulse transmission and thus disrupt the propagation of impulses from nerves to muscles. We have also found these compounds to be extremely toxic at relatively low dose levels in various animals.

The object of this invention is to synthesize new lethal agents useful in chemical warfare wherein said products are well suited for industrial scale manufacture.

Our compounds may be employed in any munition suitable for handling a relatively non-volatile toxic agent such as bombs, shells, spray tanks, rockets, missiles, aerosol generators, and others.

Other objects of and uses of the invention will be obvious from the following detailed description.

In accordance with our invention, a solution of 2-dimethylaminomethyl-3-dimethylcarbamoxypyridine and 1,10-dibromodecane (in excess) in either was refluxed for a few days. The solid that gradually formed during this interval was collected on a filter and then dissolved in acetone. The acteone solution was treated with decolorizing carbon, filtered, and then concentrated. The addition of ether produced a precipitate which solidified when the mixture was chilled overnight. The product was collected and further purified by recrystallization from ethyl acetate.

The new compounds of our invention, quaternary ammonium carbamates, may be represented by the following generic formula:

$$\begin{array}{c} \text{pyridine ring with substituents:} \\ \text{3-position: } O-C(=O)-N(CH_3)_2 \\ \text{2-position: } CH_2-\overset{\oplus}{N}(CH_3)_2-(CH_2)_{10}-Br \\ X^{\ominus} \end{array}$$

where X is one equivalent of an anion selected from monovalent and polyvalent.

The procedure used for the preparation of the new toxic materials is schematically shown as follows:

$$\text{2-dimethylaminomethyl-3-dimethylcarbamoxypyridine} + Br-(CH_2)_{10}-Br \longrightarrow$$

$$\text{quaternary ammonium bromide} \xrightarrow{\text{ion exchange}}$$

-continued

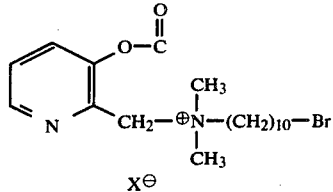

where X is a halide anion, preferably bromide.

If compounds are desired in which X is other than a halide ion, the above quaternary compounds are treated with the desired acid by simple exchange reaction as set forth below.

METHOD OF PREPARATION

A solution of 62.3 gm of 2-dimethylaminomethyl-3-dimethylcarbamoxypyridine and of 251 gm of 1,10-dibromodecane in 1 liter of anhydrous ether was refluxed for 7 days. The product that formed was collected on a filter, washed with two 100-ml portions of anhydrous ether, and dissolved in 1 liter of acetone. The acetone solution was treated with decolorizing carbon and filtered. The filtrate was concentrated under reduced pressure (about 200 mm) to approximately 200 ml. Ether was added until the solution became turbid. The mixture was then seeded and chilled overnight. The resultant crystalline product was collected and further purified by recrystallization from ethyl acetate. The pure product, N-(10-Bromodecyl)-N-(3-dimethylcarbamoxy-α-picolinyl)-N,N-dimethylammonium bromide, was dried in vacuo for 2 hours, yielding 76 gm (52%) of material mp 90° to 92° C.

Analysis of $C_{21}H_{37}Br_2N_3O_2$: Calculated: C, 48.2; H, 7.1; $Br^-$ (ionic), 15.3; O, 6.1. Found: C, 48.2; H, 7.0; $Br^-$ (ionic), 15.2; O, 6.2.

| Toxicity Intravenous $LD_{50}$ | |
|---|---|
| Rabbits | Mice |
| 0.080 mg/kg | 0.045 mg/kg |

A representative example of the compounds of our invention which is generically described above is named: N-(10-Bromodecyl)-N-(3-dimethylcarbamoxy-α-picolinyl)-N,N-dimethylammonium bromide.

We have shown a preferred compound in which the anion is limited to the halogen moiety, in particular the bromide, since the bromoalkanes are readily available and are good quaternizing agents. In general, however, it is only necessary that the anions meet the requirement of being capable of forming a stable salt with the quaternary nitrogen. Thus, the halogen ions can be exchanged with other anions of a relatively strong acid selected from monovalent and polyvalent by conventional methods. For example, if X is a bromide in the final product, a solution of the compound can be treated with a basic ion exchange resin or mixed with silver oxide and subsequently the desired acid is added to the quaternary hydroxide solution. Anions other than the halogens may also be obtained by metathesis with the halide form of the quaternary ammonium compound. Suitable as representations of $X^-$ are the anions hydrogen oxalate, perchlorate, hydrogen sulfate, nitrate, and tetraphenylboronate. Representative examples of these additional monovalent or polyvalent end products are:

N-(10-Bromodecyl)-N-(3-dimethylcarbamoxy-α-picolinyl)-N,N-dimethylammonium hydrogen oxalate.

N-(10-Bromodecyl)-N-(3-dimethylcarbamoxy-α-picolinyl)-N,N-dimethylammonium perchlorate.

N-(10-Bromodecyl)-N-(3-dimethylcarbamoxy-α-picolinyl)-N,N-dimethylammonium hydrogen sulfate.

N-(10-Bromodecyl)-N-(3-dimethylcarbamoxy-α-picolinyl)-N,N-dimethylammonium nitrate.

N-(10-Bromodecyl)-N-(3-dimethylcarbamoxy-α-picolinyl)-N,N-dimethylammonium tetraphenylboronate.

We claim:

1. Chemical compounds having the generic formula:

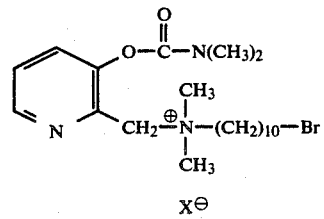

wherein X is one equivalent of an anion selected from the group consisting of monovalent and polyvalent anions, said anions being selected from the group consisting of halide, hydrogen oxalate, perchlorate, hydrogen sulfate, nitrate, and tetraphenylboronate.

2. Chemical compound having the name N-(10-Bromodecyl)-N-(3-dimethylcarbamoxy-α-picolinyl)-N,N-dimethylammonium bromide.

3. A method of producing a chemical compound having the generic formula:

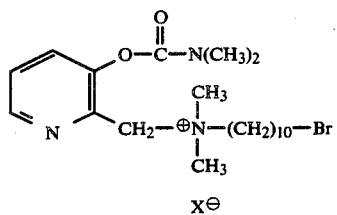

wherein X is one equivalent of an anion selected from the group consisting of monovalent and polyvalent anions, comprising the steps of making a solution of 2-dimethylaminomethyl-3-dimethylcarbamoxypyridine and excess of 1,10-dibromodecane in anhydrous ether; refluxing said solution; filtering the refluxed solution to obtain the product which formed; washing the product with anhydrous ether; dissolving the product in acetone; treating the product-acetone solution with decolorizing carbon; filtering the product-acetone decolorizing solution; concentrating the filtrate of the product-acetone decolorizing solution at a reduced pressure; adding ether until the concentrated solution became turbid; seeding the turbid solution; chilling the turbid solution until a crystalline product is formed; purifying the crystalline product by recrystallization.

* * * * *